US009427459B2

(12) United States Patent
Mohan et al.

(10) Patent No.: US 9,427,459 B2
(45) Date of Patent: Aug. 30, 2016

(54) SYNERGISTIC PHARMACEUTICAL COMPOSITION FOR TOPICAL APPLICATIONS

(75) Inventors: Vadrevu Krishna Mohan, Hyderabad (IN); Venkata Cherish Babu Pelluri, Hyderabad (IN); Khajesh Sharma, Hyderabad (IN)

(73) Assignee: Bharat Biotech International Limited (IN)

( * ) Notice: Subject to any disclaimer, the term of this patent is extended or adjusted under 35 U.S.C. 154(b) by 0 days.

(21) Appl. No.: 13/701,066

(22) PCT Filed: Jul. 14, 2010

(86) PCT No.: PCT/IN2010/000468
§ 371 (c)(1),
(2), (4) Date: Nov. 30, 2012

(87) PCT Pub. No.: WO2011/151835
PCT Pub. Date: Dec. 8, 2011

(65) Prior Publication Data
US 2013/0085103 A1    Apr. 4, 2013

(30) Foreign Application Priority Data

Jun. 3, 2010   (IN) .......................... 1534/CHE/2010

(51) Int. Cl.
| | |
|---|---|
| *A61K 38/18* | (2006.01) |
| *A61K 31/155* | (2006.01) |
| *A61K 31/555* | (2006.01) |
| *A61K 9/00* | (2006.01) |
| *A61K 9/06* | (2006.01) |
| *A61K 31/345* | (2006.01) |
| *A61K 31/635* | (2006.01) |
| *A61K 31/70* | (2006.01) |
| *A61K 33/18* | (2006.01) |
| *A61K 33/38* | (2006.01) |
| *A61K 38/12* | (2006.01) |
| *A61K 45/06* | (2006.01) |

(52) U.S. Cl.
CPC ......... *A61K 38/1858* (2013.01); *A61K 9/0014* (2013.01); *A61K 9/06* (2013.01); *A61K 31/155* (2013.01); *A61K 31/345* (2013.01); *A61K 31/555* (2013.01); *A61K 31/635* (2013.01); *A61K 31/70* (2013.01); *A61K 33/18* (2013.01); *A61K 33/38* (2013.01); *A61K 38/12* (2013.01); *A61K 38/1808* (2013.01); *A61K 45/06* (2013.01)

(58) Field of Classification Search
None
See application file for complete search history.

(56) References Cited

U.S. PATENT DOCUMENTS

2005/0281762 A1 * 12/2005 Modak et al. ................. 424/59

FOREIGN PATENT DOCUMENTS

| WO | 2004-064880 | 8/2004 |
|---|---|---|
| WO | WO 2006/126212 | * 11/2006 |

OTHER PUBLICATIONS

Cuttle et al., Burns, 33:701-707, 2007.*
Brown et al., New England Journal of Medicine, 321(2):76-79, 1989.*
Eming, S.A., Smola, H., Krieg, T., "Treatment of Chronic Wounds: State of the Art and Future Concepts" Cells Tissues Organs, vol. 172, No. 2, Jan. 1, 2002, pp. 105-117.
Modak, S., Fox, C.L., Jr., "Synergistic Action of Silver Sulfadiazine and Sodium Piperacillin on Resistant Pseudomonas Aeruginosa in Vitro and in Experimental Burn Wound Infections" Journal of Trauma, vol. 25, No. 1, Jan. 1, 1985, pp. 27-31.
Clarke, A.M., Solomon, J., Keogh, J., Nixon. M., Burchett, J., "Chlorhexidine with Silver-Sulphadiazine in the Treatment of Burns" The Medical Journal of Australia, vol. 2, No. 8, Aug. 21, 1971, p. 446.
Richards, R. M. E., Xing, D. K. L., "Evaluation of Synergistic Effects of Combinations of Antibacterials having Relevance to Treatment of Burn Wound Infections" International Journal of Pharmaceutics, vol. 75, pp. 81-88, Apr. 2, 1991.
Martinez, A., Lopez, L. D., Perez, R., Anton, J., Aguero, M. M. Peon, O., Taquechel, L., de Cespedes, V., Perez, L., Martinez, E., Dominguez, F., Lau, E. F. U., Hernandez, F., Gonzalez, T., Saura, P. A. L., Bernal, F. H., "Use of Human Recombinant Epidermal Growth Factor in Silver Sulfadiazine Cream in the Treatment of Burned Patients" Biotecnologia Aplicada, vol. 11, No. 3, 1994, pp. 209-212.

* cited by examiner

*Primary Examiner* — Marianne P Allen
(74) *Attorney, Agent, or Firm* — Roger D. Emerson; Emerson Thomson & Bennett, LLC (57) ABSTRACT

A synergistic pharmaceutical composition for the preparation of topical formulations for use in prophylaxis and treatment of wounds, burn wounds, skin grafts, pressure ulcers, diabetic foot ulcers and other skin diseases is provided. The composition may include one or more synergistically active ingredients and one or more inactive ingredients. The synergistically active ingredients may include Recombinant Human Epidermal Growth Factor (rh-EGF) (REGEN-D™ of Bharat Biotech International Limited) and/ or Platelet Derived Growth Factor (rh-PDGF-BB), silver sulfadiazine (SSD) and chlorhexidine gluconate (CHG). One or more inactive ingredients may comprise carriers, preservatives, emulsifiers, skin emollients and soothers and one or more other constituents.

15 Claims, 4 Drawing Sheets

Range of percentage of wound healing of burn patients

Effect of novel formulations on *Staphylococcus aureus*. Control [■], rh-EGF of BBIL and SSD combination[♦] and rh-EGF of BBIL, SSD and CHG [▲].

SYNERGISTIC PHARMACEUTICAL COMPOSITION FOR TOPICAL APPLICATIONS

FIELD OF THE INVENTION

The invention relates to a novel synergistic pharmaceutical composition for topical applications. More particularly, the invention relates to a novel synergistic pharmaceutical composition for the preparation of topical formulations for use in prophylaxis and treatment of wounds, burn wounds, skin grafts, pressure ulcers, diabetic foot ulcers and other skin diseases. The novel formulation of the invention comprises one or more synergistically active ingredients and one or more inactive ingredients. The synergistically active ingredients comprise a mitogenic protein (growth factor) in synergistic combination with one or more bactericidal and bacteriostatic agents. More particularly, the synergistically active ingredients comprise Recombinant Human Epidermal Growth Factor (rh-EGF) (REGEN-D™ of Bharat Biotech International Limited) and/or Platelet Derived Growth Factor (rh-PDGF-BB), silver sulfadiazine (SSD) and chlorhexidine gluconate (CHG) whereas, one or more inactive ingredients may comprise carriers, preservatives, emulsifiers, skin emollients and soothers and one or more other constituents. The novel composition of the invention may be used for the preparation of topical formulations for application on wounds, burn wounds, skin grafts, pressure ulcers, diabetic foot ulcers and other skin diseases either in the form of a cream or gel or liquid form.

BACKGROUND OF THE INVENTION

Burn is any extremity experienced by the skin caused by heat, cold, electricity, chemicals, friction or radiation. Burn injury is generally associated with tissue fluid and electrolyte imbalance, decelerated healing of the burnt area, metabolic disturbance, muscle catabolism and various other complications of vital organs and may further have secondary complications like infection by bacteria and/or microorganisms. Each of these complications needs different agents/drugs to provide a comprehensive burn management in saving the life.

Burns related injuries and death is a major problem in South East Asia, especially in developing countries like India. As per WHO reports, South East Asia region contributes towards 10% of global burden, with India alone accounting for 35,000 burn related deaths annually. Even in a developed country such as USA, an estimated 2.1 million Americans seek medical treatment each year for burns. One of the major causes of mortality in burn patients is severe systemic infection. The primary route of entry of these infections is the exposure of raw burn surface to various bacteria and pathogens. Factors, such as disruption of the skin barrier, a large cutaneous bacterial load, the possibility of the normal bacterial flora turning into opportunistic pathogens and the severe depression of the immune system contribute towards sepsis in a burns victim, which usually is life threatening [1]. Appropriate wound management of burn surface and early re-epitheliazation with wound closure is a vital step in the treatment and prognosis of burn patients.

Infection control is a very important process in the prevention of secondary infections and also in maintaining a proper burn wound healing process. Although the use of topical antimicrobial agents is essential in the establishment of the bacterial balance in burn wounds, it has been associated with delayed healing of burn wounds in which the process of skin proliferation and collagen deposition play a major role [2]. Some studies showed that the wound healing process is delayed, which is significant with second and third degree burns, due to delayed or less production of growth promoting factors like Recombinant Human Epidermal Growth Factor (rh-EGF) or Platelet Derived Growth Factor (rh-PDGF-BB) using their receptors.

Recombinant Human Epidermal Growth Factor rh-EGF belongs to a family of growth factors that regulate cell proliferation, migration and differentiation through binding to receptor kinase on target cells [3]. rh-EGF has been shown to act as a potent mitogen and also as a differentiation factor for many cell types including smooth muscle cells [4]. Experimental studies in animals have demonstrated that topical application of rh-EGF accelerates the rate of epidermal regeneration of partial thickness wounds and second degree burns [5]. rh-EGF is 53 amino acids protein with a molecular weight of 6.2 kDa and is obtained by recombinant gene technology. A novel vector was constructed encoding synthetic rh-EGF polynucleotide sequence, which was overexpressed in E. coli and purified to obtain >98% pure protein [6].

In the process of wound healing the signal for cellular proliferation is given by rh-EGF peptide via EGF receptors. The EGF receptors have tyrosine kinase transmembrane domains, with a cytoplasmic domain and extra cellular domain, which are involved in rh-EGF binding. This results in EGF receptor dimerization, autophosphorylation of the receptor and tyrosine phosphorylation of other proteins. This activates mitogen activated protein kinase (MAP kinase) pathway, ultimately causing phosphorylation of transcription factors such as C-Fs to create AP-1 and ELK-1 that contribute to proliferation. Activation of STAT-1 and STAT-3 transcription factors by JAK kinase in response to rh-EGF contribute to proliferative signalling. Further, phosphatidylinositol signalling and calcium release induced by rh-EGF active protein kinase C is another component of EGF signalling. The above process attracts cells into wounds and stimulates their proliferation, enhances the rate of formation of granulation tissue and increase collagen production [7, 8].

Though the growth factors like rh-EGF help in healing the burn wounds, it is important to prevent the infection caused during burn wound management. Recombinant human epidermal growth factor rh-EGF (REGEN-D, Bharat Biotech International Limited), which was cloned and over expressed in E. coli, has shown enhanced healing of burn wounds by significantly reducing the duration of healing. But the risk associated with burn wounds is invasion of infection by micro-organisms. This is where the antimicrobial agents play significant role in burn wound management.

In the prior art, various topical antibacterial/antimicrobial agents are available for wound care like Bacitracin, Polymyxin B sulfate, Neomycin, Povidone-iodine, Mafenide acetate cream, Nitrofurazone, Gentamicin etc.

Bacitracin is a polypeptide antibiotic that is effective against Gram-positive cocci and bacilli. Bacitracin may also enhance re-epithelialization of the wound, though it has no affect on keratinocyte proliferation. Incidence of resistant strains is unlikely to increase because bacitracin acts on the properties of the bacterial plasma membrane and not on molecular synthesis [9].

Polymyxin B sulfate is a simple basic peptide antibiotic that is effective against Gram-negative organisms. Polymyxin B sulphate causes a greater reduction of keratinocyte proliferation [10].

Neomycin is broad-spectrum antibiotic and is particularly effective against Gram-negative organisms. However, side effects like hypersensitivity reactions, particularly skin rashes occur more frequently with neomycin [11].

Povidone-iodine is a bactericidal effective against Gram-positive and Gram-negative bacteria. Povidone-iodine at clinical concentration has been shown to be toxic to human fibroblasts and keratinocytes in vitro. Povidine-iodine has also been reported to be inactivated by wound exudates. This topical agent may harden wound eschar rather than soften it, thus increasing the difficulty and discomfort of wound debridement [1].

Mafenide acetate is a methylated topical sulfonamide compound. This drug has wide range of antibacterial activity against most Gram-negative and Gram-positive pathogens. However, use of mafenide may be inhibitory to re-epithelialization. Mafenide suppresses Polymorphonuclear Leukocytes (PMN) and lymphocyte activity [16].

Nitrofurazone compound is abroad spectrum antibacterial effective against *S. aureus, Enterobactor* and *E. coli*, but it is less effective against *P. aeruginosa* and has no significant fungicidal activity. Nitrofurazone has been shown to have a detrimental effect on the growth and migration of keratinocytes in culture [17]. Nitrofurazone is not frequently used in burn centres in the United States.

Gentamicin is very effective against Gram-negative micro-organisms. Resistance to gentamicin may be developed and this resistance certainly limits the usage of this medication. Gentamicin has been shown to inhibit the activity of PMNs. Skin hypersensitivity has been reported with gentamicin [20].

Silver sulfadiazine (SSD) is a topical sulfonamide compound of silver nitrate and sodium sulfadiazine prepared as 1% water miscible cream. Silver sulfadiazine is effective against a wide range of flora, particularly Gram-negative bacteria like *E. coli, Enterobacter, Klebsiella* species, *P. aeruginosa* and Gram-positive bacteria like *S. aureus* and *Candida albicans*.

Amongst the various topical antimicrobial agents available for the burn wounds, some of them specified above, sulphonamide derivatives have enjoyed a well deserved reputation in recent years for the treatment of different degrees of burn wounds infected with Gram-positive and Gram-negative bacterial infections as well as being effective against yeast. Amongst sulphonamides, the drug of choice for prophylaxis and treatment in most burn patients has been silver sulfadiazine (SSD). SSD is an effective broad spectrum antimicrobial agent commonly incorporated into topical creams used for burn wounds. In fact, since last five decades. SSD has been traditionally used for the treatment of different degrees of burn wounds infected with micro-organisms.

Past studies have shown that SSD inhibits bacteria that are resistant to other antimicrobial agents and that the compound is superior to many other antimicrobial agents. It acts on the cell membrane and cell wall of micro-organisms to produce its bactericidal effect. Silver is slowly released from the preparation in concentrations that are selectively toxic to bacteria. Silver also damages the DNA of the bacteria cell. Sulfadiazine, like other sulphonamides, inhibits bacterial synthesis of dihydrofolic acid by competing with para-aminobenzoic acid (PABA). It does not act on human cells.

Another antimicrobial agent namely chlorhexidine gluconate (CHG) is a powerful, relatively non-toxic antiseptic which has found widespread approval in current clinical practice [18]. CHG is an important antiseptic, disinfectant, antibacterial dental rinse, and preservative. It has wide antimicrobial spectrum and is effective against Gram-positive. Gram-negative bacteria, viruses and fungi. CHG binds to bacterial cell wall and cytoplasmic components leading to altered osmotic equilibrium and also precipitation of cytoplasmic components. At low concentrations, chlorhexidine is bacteriostatic; at higher concentrations, it is bactericidal. Chlorhexidine gluconate is a bisbiguanide that binds to the stratum corneum, providing sustained bactericidal and fungicidal activity. It does not lose its effectiveness in the presence of organic material, such as whole blood. CHG gets adsorbed onto the cell walls of microorganisms causing leakage of absorbing material from a wide variety of bacteria and affects the structure of proteins, inhibiting for example, membrane-bound ATPase [19], altering the configuration of proteins and facilitating the uptake of polymyxin by cells.

Though SSD is a standard treatment for burn wounds for the last fifty years, some studies showed that the compound delays the wound healing process, which is significant with second and third degree burns, due to delayed or less production of growth promoting factors using their receptors. Also, the absorption of silver from burn wounds led to silver toxicity leading to the impairment of dermal regeneration and decreased mechanical strength of dermal tissue. Several in vitro studies with human dermal fibroblasts have shown progressive cellular cytotoxicity with increasing concentrations of SSD and mafenide acetate. In the same studies the pre exposure of human dermal fibroblasts to EGF, basic fibroblast growth factor, or platelet-derived growth factor has resulted in cytoprotection of human dermal fibroblasts against effect of SSD [29].

Cases of bacterial resistance to silver have also been reported. Cason et al reported this in Gram-negative bacilli in burn wounds as early as 1966 [21]. In the late 1970s there were several reports of outbreaks of burn wound infection or colonisation by Gram-negative isolates resistant to SSD (*Enterobacter cloacae, Providencia stuartii*, and *P. aeruginosa*). It is clear that exposure to silver might select resistant micro-organisms and this could play important part in the predominance of intrinsically silver-resistant bacteria where silver is widely used.

Li et al reported the development of bacterial resistance to high concentration of silver (>1024 ppm) by repeated exposure to increasing concentrations in vitro [27].

The drawbacks related to the use of SSD for the treatment of burn wounds led to development of a formulation by Bharat Biotech International Limited (BBIL) comprising SSD with rh-EGF. This combination helps in the release of rh-EGF for a prolonged period and limitation of the delivery of silver necessary for optimum wound healing effect. The most important function of this SSD and rh-EGF combination is cytoprotective effect of rh-EGF against SSD and also helping in reversibility of the impaired burn wound healing process by the co-supplementation of EGF. The results established that this combination helps in reversal of cytotoxic effect of silver there by hastening wound healing process in burn patients. But concern has been raised regarding the potential for development of bacterial resistance against SSD and silver-resistant organisms reported in clinical samples due to permeability barrier.

Studies were done for the permeability of EGF into blood stream using rh-EGF of BBIL and SSD combination, and the results were found negative, which clearly showed that rh-EGF produced at BBIL doesn't enter into the blood stream. The combination of SSD with rh-EGF of BBIL trials in burn patients showed the effectiveness of the application of rh-EGF on the acceleration of the cicatrization process of dermal and hypodermal burns, resulting in a skin with an appearance, elasticity and colour identical to the normal skin and the major achievement being without hypertrophic scars. These evidences show the effect of rh-EGF on cicatrization, possibly due to its mitogenic effect.

Though the combination of rh-EGF and SSD had taken care of the delayed wound healing problem by reversal of SSD effect, the most important drawback in this formulation is that sulphonamide resistance is frequently noticed due to impermeable ability of SSD. Despite the medical benefits of using ionic silver to manage infections, concern has been raised regarding the potential for development of bacterial resistance and an association with cross-resistance to antibiotics has been implied. Silver-resistant organisms have been reported in clinical and environmental samples. The combination of SSD with EGF can only prevent the cytotoxic effect due to silver and helps in reversal of the impaired wound healing process. But this combination cannot be effective against the micro-organisms resistance against SSD due the permeability barrier. This combination is not sufficient in prevention of infection against the micro-organisms resistant to silver and this can lead to the cause of secondary infection which may prolong the wound healing process and also a serious threat to the burn wounds.

In the prior art a large number of antimicrobial agents have been tested and used. One of the most common agent among them have been the silver sulfadiazine (SSD) which has been used as alone or in combination with other antimicrobial agents like chlorhexidine gluconate (CHG) or a combination of SSD with rh-EGF as used by Bharat Biotech International Limited.

However, none of the prior art formulations were able to provide a much broader spectrum coverage, quicker wound healing without the risk of resistance development, metal ion toxicity, cytotoxicity etc.

OBJECT OF THE INVENTION

The primary object of the invention is to provide a broad spectrum pharmaceutical composition for preparation of topical formulations to be used for prophylaxis and treatment of wounds, burn wounds, skin grafts, pressure ulcers, diabetic foot ulcers and other skin diseases.

Another object of the invention is to provide a novel topical pharmaceutical formulation comprising antimicrobial/antibacterial agents and mitogenic proteins with a broader antibacterial/antimicrobial spectrum and which is effective against SSD resistant micro-organisms with no or negligible side effects.

Another object of the invention is to provide a novel topical pharmaceutical formulation with better and faster wound healing properties with any one of the growth factors.

Further object of the invention is to provide a novel broad spectrum topical pharmaceutical formulation, in the form of cream, gel or liquid, which has longer stability and shelf life.

SUMMARY OF THE INVENTION

A novel synergistic broad spectrum pharmaceutical composition for preparation of topical formulations for prophylaxis and treatment of wounds, burn wounds, skin grafts, pressure ulcers, diabetic foot ulcers and other skin diseases is disclosed, wherein the formulation may be in the form of cream, gel or liquid.

The novel synergistic composition of the invention comprises at least three synergistically active ingredients and one or more inactive ingredients. The synergistically active ingredients comprise one or more broad spectrum bactericidal agent, one or more broad spectrum bacteriostatic agent and a mitogenic growth factor.

The inactive ingredients are used to provide a base, permeability and stability to the formulation and comprise carriers, preservatives, emulsifiers, skin emollients and soothers and one or more other constituents.

In one preferred embodiment of the invention, the mitogenic protein is Recombinant Human Epidermal Growth Factor (rh-EGF) developed by Bharat Biotech International Limited (REGEN-D™) or Platelet Derived Growth Factor (rh-PDGF-BB)

The bactericidal and bacteriostatic agents are selected from the group consisting of bacitracin, silver sulfadiazine (SSD), nitrofurazone, chlorhexidine gluconate (CHG), polymyxine B sulphate, neomycine, povidone-iodine, mafenide, nitrofurazone and gentamicin.

In the preferred embodiment of the invention the broad spectrum bactericidal agent is silver sulfadiazine (SSD) and broad spectrum bacteriostatic agent is chlorhexidine gluconate (CHG).

The synergistically inactive ingredients of the formulation are selected from the group consisting of PEG-30 dipolyhydroxystearate, isohexadecane. C-12-15 alkyl benzoate, titanium dioxide, polyhydroxystearic acid, aluminium stearate, alumina, magnesium sulphate, stearic acid, sorbitol, methylparaben sodium, propylparaben sodium, sodium hydroxide, disodium EDTA, ammonium acryloyldimethyltaurate/VP copolymer, dipalmitoyl hydroxyproline, Bois II™, cetyl alcohol, C12-15 alkyl benzoate, caprylic/capric triclyceride, tocopheryl acetate, polyacrylamide, C13-14 isoparaffin, ethoxydiglycol, phenoxyethanol, methyl, butyl, ethyl & propylparaben, triethanolamine, light liquid paraffin, pemulen TR-1, carbopol ultrez, mannitol, and Purified water.

The novel synergistic composition of the invention has synergistic effects like broader antimicrobial and/or antibacterial spectrum, effectiveness against SSD resistant micro-organisms, better and faster wound healing, reversal of the SSD cytotoxicity, longer stability and shelf life of the formulation with sustained antibacterial/antimicrobial activities.

Various trials and test results have shown that this composition is best suitable for different degrees of burn wounds and this novel synergistic composition can also be used for other indications like wounds, skin grafts, pressure ulcers and diabetic foot ulcers.

Results from the studies clearly indicated that the novel formulation was very effective in different degrees of burns and also for quick healing of the burns without any infection. Stability studies were conducted for these novel formulations, both real time and accelerated time stability studies of this novel formulation have shown that the combination was stable and more efficacious in quick healing of burn wound without any infection.

The novel synergistic composition of the formulation comprising rh-EGF, silver sulfadiazine (SSD) and chlorhexidine gluconate (CHG) prevents the effect of micro-organisms resistant to silver and helps in the permeability of silver in burn wounds. The CHG even in low concentrations in the formulation helps in permeability of silver in burn wounds thereby enhances the effectiveness of silver against the resistant micro-organisms.

The rationale of the choice of this synergistic combination of rh-EGF of BBIL. SSD and CHG was that sulphonamide resistance is frequently due to a permeability barrier and chlorhexidine is well known to be able to affect this barrier, secondly the combination has prophylactic properties in burn therapy comparable with those of SSD and resistance does not emerge to either of the former and the wound healing process is faster with the three agents of the formulation than the rh-EGF+SSD alone.

This novel synergistic composition helps in reversal of silver effect by rh-EGF and is also effective against wide spectrum of microorganisms resistant to silver, wherein this resistance is prevented by increasing the permeability of silver by the addition CHG in low concentrations. The synergistic results of the composition are obtained due to synergistic interaction between CHG and SSD. The CHG of the formulation increases the antibacterial effectiveness of SSD. Further, the micro-organisms resistant to extremely high concentration of SSD may also be killed when SSD is used in combination with CHG in the formulation of the present invention. The resistance of some species of *Pseudomonas* and *Staphylococcus* strains to sulphonamide is due to a barrier mechanism as explained in above paragraphs. But with CHG and SSD combination, it is concluded that CHG does not alter the membrane sufficiently to permit the efflux of nitrogen bases, nucleotides or nucleosides, the alteration is sufficient to permit the entry of sulphadizine molecules, thereby allowing the complete reduction of micro-organisms in the burn wounds.

Therefore, the synergistic effect of CHG and SSD along with rh-EGF of BBIL in the novel formulation of the present invention provides most effective control of infection in burn wounds by topical prophylactic action as well as for treatment.

DETAILED DESCRIPTION

Detailed embodiments of the present invention are disclosed herein however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The invention relates to a novel synergistic broad spectrum pharmaceutical composition for preparation of topical formulations in the form of cream or gel or liquid for prophylaxis and treatment of wounds, burn wounds, skin grafts, pressure ulcers, diabetic foot ulcers and other skin diseases.

The novel synergistic composition of the invention comprises at least three synergistically active ingredients and one or more inactive ingredients. The synergistically active ingredients comprise one or more broad spectrum bactericidal agent, one or more broad spectrum bacteriostatic agent and a mitogenic growth factor.

The inactive ingredients are used to provide a base, permeability and stability to the formulation and comprise carriers, preservatives, emulsifiers, skin emollients and soothers and one or more other constituents.

In one preferred embodiment of the invention, the mitogenic protein is Recombinant Human Epidermal Growth Factor (rh-EGF) developed by Bharat Biotech International Limited (REGEN-D™) or a growth factor like Platelet Derived Growth Factor (rh-PDGF-BB).

The bactericidal and bacteriostatic agents are selected from the group consisting of bacitracin, silver sulfadiazine (SSD), nitrofurazone, chlorhexidine gluconate (CHG), polymyxine B sulphate, neomycine, povidone-iodine, mafenide, nitrofurazone and gentamicin.

In the preferred embodiment of the invention, selected broad spectrum bactericidal agent is silver sulfadiazine (SSD) and broad spectrum bacteriostatic agent is chlorhexidine gluconate (CHG).

The synergistically inactive ingredients of the formulation are selected from the group consisting of PEG-30 dipholyhydroxystearate, isohexadecane, C-12-15 alkyl benzoate, titanium dioxide, polyhydroxystearic acid, aluminium stearate, alumina, magnesium sulphate, stearic acid, sorbitol, methylparaben sodium, propylparaben sodium, sodium hydroxide, disodium EDTA, ammonium acryloyldimethyl-taurate/VP copolymer, dipalmitoyl hydroxyproline, Bois II™, cetyl alcohol, C12-15 alkyl benzoate, caprylic/capric triglyceride, tocopheryl acetate, polyacrylamide, C13-14 isoparaffin, ethoxydiglycol, phenoxyethanol, methyl, butyl, ethyl & propylparaben, triethanolamine, light liquid paraffin, pemulen TR-1, carbopol ultrez, mannitol, and Purified water. In one preferred embodiment of the invention, the novel synergistic composition comprises a mitogenic protein (rh-EGF), a bactericidal agent (SSD) and a bacteriostatic agent (CHG) in the desired ratio producing synergistic effects like broader microbial and/or bacterial coverage, effectiveness against silver resistant micro-organisms, better and faster wound healing, reversal of the SSD cytotoxicity, reversal of silver effect of SSD, and longer shelf life of the formulation with sustained antibacterial/antimicrobial activities.

Recombinant Human Epidermal Growth Factor (rh-EGF) (REGEN D of Bharat Biotech International Limited) is a well known growth factor which has been used for treatment and management of the indications like wounds, skin grafts, burns wounds, pressure ulcers and diabetic foot ulcers. rh-EGF belongs to a family of growth factors, which is known to regulate cell proliferation, migration and differentiation. rh-EGF has been shown to act as a mitogen and also as a differentiation factor for many cell types. Although rh-EGF helps in healing of the wounds it is important to prevent the infection during burn wound management.

SSD is a standard treatment for burns. But some studies showed that the compound delays the wound healing process, which is significant with second and third degree burns, due to delayed or less production of growth promoting factors using their receptors.

To prevent the effect of silver resistant micro-organisms and to help in the permeability of silver against resistant micro-organisms, the novel formulation of the present invention has been developed, wherein to the combination of SSD and rh-EGF, an additional agent CHG is added. The rationale behind the combination being CHG even in low concentrations helps in permeability of silver to resistant micro-organisms in burn wounds, thereby helping the effectiveness of silver against the resistant micro-organism.

Chlorhexidine gluconate is a bisbiguanide that binds to the stratum corneum, providing sustained bactericidal and fungicidal activity for over 6 hours, even when wiped from the field. It does not lose its effectiveness in the presence of organic material, such as whole blood, it is an important antiseptic, disinfectant, antibacterial dental rinse, and preservative. It has antimicrobial spectrum against Gram-positive, Gram-negative bacteria, viruses and fungi. CHG binds to bacterial cell wall and cytoplasmic components leading to altered osmotic equilibrium and also precipitation of cytoplasmic components.

The results established using this novel synergistic composition has shown reversal of silver effect by preventing the cytotoxicity of silver with the addition of rh-EGF. Addition of CHG made this novel combination effective against a wide spectrum of micro-organisms by increasing the permeability of silver to the resistant micro-organisms.

This novel synergistic formulation also showed the effect on reduction of micro-organism in their combination in in vitro analysis, wherein this synergistic combination was effective against a wide spectrum of antibiotic resistant micro-organisms. The results established that this novel synergistic composition was highly stable with a shelf life of more than two years, which is used as a topical pharmaceutical formulation for treating different degree of wounds caused by burns and also for other indications like wounds, skin grafts, pressure ulcers and diabetic foot ulcers.

In the present invention, each component in the formulation was measured for its concentration using the standard available methods. The efficacy of rh-EGF was decided by performing animal trial with different concentration of rh-EGF starting from 5 µg, 10 µg, and 15 µg and keeping SSD and CHG at optimum concentration [Example 1] and trials in burn patients [Example 3].

The efficacy of rh-PDGF-BB was decided by performing animal trial with different concentration of rh-PDGF-BB starting from 1 µg, 3 µg, and 5 µg and keeping SSD and CHG at optimum concentration [Example 2].

rh-EGF concentration was estimated by validated ELISA method [Example 4].

For the estimation of SSD in the novel formulations, assay was performed based on the assay method available in United State Pharmacopoeia. Result of these estimation showed that exact amount of SSD added to the cream could be estimated [Example 5].

For the estimation of CHG in the novel formulations, assay was performed based on the assay method available in British Pharmacopoeia [Example 5].

This novel synergistic formulation containing rh-EGF, SSD and CHG also showed the effect on reduction of micro-organism in their combination in in vitro analysis, wherein the kinetic effects if this synergistic combination for the first time is effective against a wide spectrum of antibiotic resistant micro-organisms [Example 6].

In the present invention accelerated and real time stability studies were done for the novel formulations involving SSD, CHG and rh-EGF and the results clearly showed that the three ingredients are stable without any reduction or decrease in the added compositions of all formulations and this novel formulations is stable for more than two years.

EXAMPLES

Example 1

Selection of Different Concentrations of Rh-EGF for Testing the Efficacy in Animal Model For the novel synergistic formulation combination SSD. CHG and the addition of the third agent namely rh-EGF of BBIL was varied from 5 µg, 10 µg and 15 µg, to choose the best combination of these three agents. Stability studies were done on these novel formulations. The stable formulations were applied in the designed animal models for checking the efficacy of these novel formulations.

Eight combinations of the formulations were tested in animal models for the efficacy of the novel formulations:
1. 1% silver sulfadiazine cream
2. 1% silver sulfadiazine+rh-EGF 10 µg/g cream
3. 1% silver sulfadiazine+0.02% chlorhexidine gluconate+rh-EGF 5 µg/g cream
4. 1% silver sulfadiazine+0.02% chlorhexidine gluconate+rh-EGF 10 µg/g cream
5. 1% silver sulfadiazine+0.02% chlorhexidine gluconate+rh-EGF 15 µg/g cream
6. 1% silver sulfadiazine+0.02% chlorhexidine gluconate+rh-EGF 5 µg/g gel
7. 1% silver sulfadiazine+0.02% chlorhexidine gluconate+rh-EGF 10 µg/g gel
8. 1% silver sulfadiazine+0.02% chlorhexidine gluconate+rh-EGF 15 µg/g gel A total of 96 rats [48 males and 48 females] were selected for testing the efficacy of the novel synergistic formulations of rh-EGF. The total animal population was divided into two main groups, Group I as test group and Group II as control group. Each group was subdivided into 8 sub-groups, wherein the eight groups were applied with eight different formulation of the above said combination with varying concentration of rh-EGF starting form 5 µg/g, 10 µg/g and 15 µg/g cream and gel.

TABLE 1

Novel formulation and number of animal data.

|  | Group I (Test) | Group II (Control) |
| --- | --- | --- |
| N | 48 | 48 |
| Sex (M/F) | 24/24 | 24/24 |
| Age (Weeks) | 6-7 weeks | 6-7 weeks |

Burn Wound Creation in Animal Models:

The test and control group animals were used for creation of burn wound. Specially made brass rods were used for the creation of burn wounds in rats. The brass rods were kept in a heating water bath at 75±2° C. for 15±1 min. The animals were shaved with area of 2×2×2 cm size, previous day before start of the experiment. The brass rod was taken out from the water bath and kept on the skin of the rats for a brief time period of 15-20 sec and taken out immediately. The rod diameter was selected such a way that when the rod touches the skin of the animal should create a wound of around 1 cm. For each animal a separate sterile rod is used to prevent any infection if present in animals or any transfer of infections from one animal to the other. After 30 min of the burn wound creation on rats, the above said five novel cream based formulations were applied. Both the study formulations and the control were spread evenly on the burn area with a sterile cotton swab twice daily till the wound heels or till the end of six weeks. Prior to application, basic burn wound management if any was carried out in animals.

The primary objective of this study is the duration of healing which was significantly reduced in case of Group I by more than 40% compared to Group II. A secondary end point of epitheliazation was observed in novel formulation group compared to the control group. There is very less difference efficacy between the cream and gel formulations. The cream formulations are more efficacious in comparison with the gel formulations and both these cream and gel formulations are superior when compared with the other two normal formulations. No significant scar hypertrophy or any pigmentation changes were observed in novel formulation sub-groups from three to eight. The duration of the burn wound healing was not similar in all novel formulation animals, but the percentage of healing time was more than 50% in comparison with the control group animals.

TABLE 2

Novel formulations cohort data.

| | Group I (Test) | Group II (Control) |
|---|---|---|
| Number of animals | 48 | 48 |
| Sex (M/F) | 24/24 | 24/24 |
| Age (weeks) | 6-7 weeks | 6-7 weeks |
| Average size of the burn wound (cm) | 1 | 1 |
| Average burn wound healing (epithelialization) | 95% | 60% |
| Average duration of healing (epithelialization) | 7 days | 16 days |

Of the 96 animals tried with these novel formulations, the duration of the burn wound healing was not similar in all novel formulation animals, but the results clearly indicate that these formulations are promoting the healing time quicker than their control groups.

TABLE 3

Novel formulation cohort data.

| | Group I (Test) | Group II (Control) |
|---|---|---|
| N | 30 | 30 |
| Sex (M/F) | 15/15 | 15/15 |
| Age (Weeks) | 6-7 weeks | 6-7 weeks |
| Duration of healing (Avg. days) | | |
| Novel Formulation-1 [1% SSD cream] | 10 days [6 nos] | 16 days [6 nos] |
| Novel Formulation-2 [1% SSD + rh-EGF - 10 µg/g cream] | 8 days [6 nos] | 15 days [6 nos] |
| Novel Formulation-3 [1% SSD + 0.02% CHG + rh-EGF - 5 µg/g cream] | 7 days [6 nos] | 18 days [6 nos] |
| Novel Formulation-4 [1% SSD + 0.02% CHG + rh-EGF - 10 µg/g cream] | 5 days [6 nos] | 15 days [6 nos] |
| Novel Formulation-5 [1% SSD + 0.02% CHG + rh-EGF - 15 µg/g cream] | 5 days [6 nos] | 16 days [6 nos] |
| Novel Formulation-6 [1% SSD + 0.02% CHG + rh-EGF - 5 µg/g gel] | 8 days [6 nos] | 17 days [6 nos] |
| Novel Formulation-7 [1% SSD + 0.02% CHG + rh-EGF - 10 µg/g gel] | 6 days [6 nos] | 18 days [6 nos] |
| Novel Formulation-8 [1% SSD + 0.02% CHG + rh-EGF - 15 µg/g gel] | 6 days [6 nos] | 18 days [6 nos] |

Based on the above percentage of healing time it was concluded that the topical formulation comprising a composition of 1% SSD+0.02% CHG+10 µg/g rh-EGF cream was the best formulation to be used for burn patients. The formulation underwent both the accelerated time and real time stability studies with the said composition at temperature of +25° C.±2° C. for accelerated time and temperature of 5° C.±3° C. for real time respectively and the results established that the combination is highly stable at storage temperature of +2° C. to 8° C. for more than two years.

Figure 1:
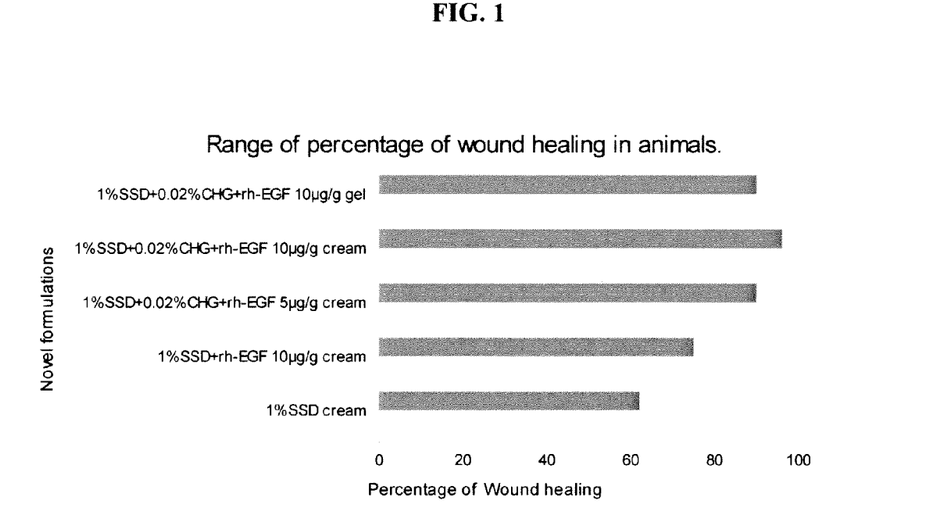
FIG. 1 is a geometrical representation showing the percentage of wound healing with respect to number of animals using different concentrations of rh-EGF in the formulations.

Referring to FIG. 1, it shows the percentage of wound healing in animals with different compositions of active ingredients i.e. rh-EGF, SSD and CHG in the formulations. The results of the cream formulations showed that wound healing percentage was only about 60% when only 1% SSD was used in the formulation. The wound healing improved to about 78% with a combination of 1% SSD and 10 µg/g of rh-EGF. The wound healing percentage was about 95% with a combination of 1% SSD, 0.02% CHG and 5 µg/g of rh-EGF. Whereas, the wound healing percentage was almost 100% with the formulation comprising 1% SSD, 0.02% CHG and 10 µg/g of rh-EGF. When compared the cream and gel formulations with the same composition, the results showed that cream formulations have slightly higher healing rate than the gel formulations.

Example 2

Selection of Different Concentrations of Rh-PDGF-BB for Testing the Efficacy in Animal Model For the novel synergistic formulation combination SSD, CHG and the addition of the third agent namely rh-PDGF-BB was varied from 1 µg/g, 3 µg/g and 5 µg/g, to choose the best combination of these three agents. These formulations were applied in the designed animal models for checking the efficacy of these novel formulations, by making the burn wound creation as explained above.

Five combinations of the formulations were tested in animal models for the efficacy of the novel formulations:
1. 1% silver sulfadiazine cream
2. 1% silver sulfadiazine+rh-PDGF-BB 5 µg/g cream
3. 1% silver sulfadiazine+0.02% chlorhexidine gluconate+rh-PDGF-BB 1 µg/g cream
4. 1% silver sulfadiazine+0.02% chlorhexidine gluconate+rh-PDGF-BB 3 µg/g cream
5. 1% silver sulfadiazine+0.02% chlorhexidine gluconate+rh-PDGF-BB 5 µg/g cream A total of 60 rats [30 males and 30 females] were selected for testing the efficacy of the novel synergistic formulations of rh-PDGF-BB. The total animal population was divided into two main groups, Group I as test group and Group II as control group. Each group was subdivided into five sub-groups, wherein the five groups were applied with five different formulation of the above said combination with varying concentration of rh-PDGF-BB starting form 1 µg/g, 3 µg/g and 5 µg/g cream.

TABLE 4

Novel formulation and number of animal data.

|  | Group I (Test) | Group II (Control) |
| --- | --- | --- |
| N | 30 | 30 |
| Sex (M/F) | 15/15 | 15/15 |
| Age (Weeks) | 6-7 weeks | 6-7 weeks |

The primary objective of this study is the duration of healing which was significantly reduced in case of Group I by more than 30% compared to Group II. The duration of the burn wound healing was not similar in all novel formulation animals, but the percentage of healing time was more than 30% in comparison with the control group animals,

TABLE 5

Novel formulations cohort data.

|  | Group I (Test) | Group II (Control) |
| --- | --- | --- |
| Number of animals | 30 | 30 |
| Sex (M/F) | 15/15 | 15/15 |
| Age (weeks) | 6-7 weeks | 6-7 weeks |
| Average size of the burn wound (cm) | 1 | 1 |
| Average burn wound healing (epithelialization) | 90% | 60% |
| Average duration of healing (epithelialization) | 9 days | 18 days |

Figure 2:
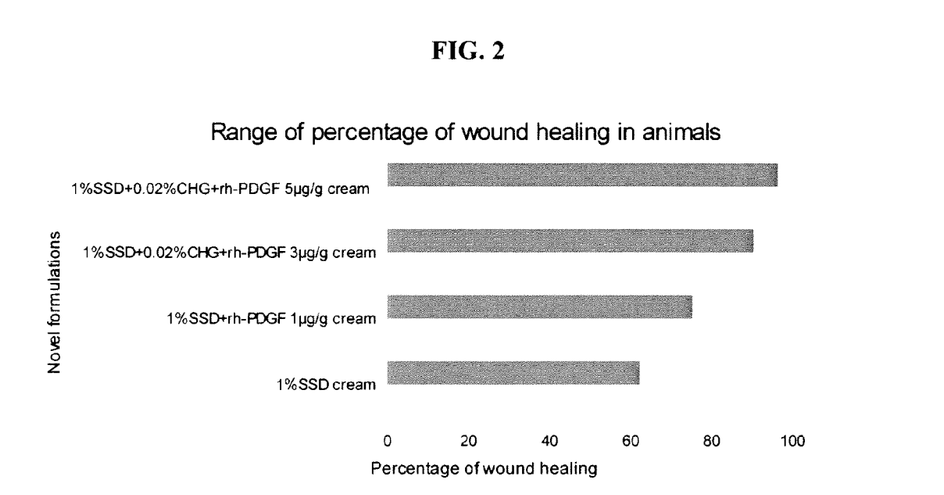
FIG. 2 is a geometrical representation showing the percentage of wound healing with respect to number of animals using different concentrations of rh-PDGF-BB in the formulations.

Referring to FIG. 2, it shows the percentage of wound healing in animals with different compositions of active ingredients i.e. rh-PDGF-BB, SSD and CHG in the formulations. The results of the cream formulation with 5 µg/g rh-PDGF-BB, SSD and CHG showed wound healing percentage better when compared to the other groups.

Example 3

Safety and Efficacy of Novel Formulations in Burn Patients

Several growth factors like EGF, FGF, and TGF have been identified as regulatory proteins, which coordinate the healing process and participate in the regulation of cell proliferation, differentiation and organ growth. Various human studies have been carried out to evaluate acceleration of burn wound healing with topical application of rh-EGF ointment. Five combinations of the formulations were tested in burn patients for the efficacy of the novel formulations:
1. 1% silver sulfadiazine (Control)
2. 1% silver sulfadiazine+rh-EGF 10 µg/g (Group I)
3. 1% silver sulfadiazine+0.02% chlorhexidine gluconate+rh-EGF 5 µg/g (Group II)
4. 1% silver sulfadiazine+0.02% chlorhexidine gluconate+rh-EGF 10 µg/g (Group III)
5. 1% silver sulfadiazine+0.02% chlorhexidine gluconate+rh-EGF 15 µg/g (Group IV)

In the present study, a novel synergistic formulation comparative study was done to evaluate the safety and efficacy of these formulations versus control group in superficial (First degree-affect only outer layer of the skin) and partial thickness (Second degree—affect both the outer and underlying layers of skin) of burn patients. A total of 50 patients which included both male and female were recruited to both the groups—Group I to Group IV (novel combinations) with 40 patients and control group with 10 patients. To evaluate and compare the proportion of subjects with complete wound closure in the test group to control group, in burn patients, with the following parameters:

(a) Rate of healing (by measurement of wound healing).

(b) Time required for complete wound closure (number of days).

A sterilized transparent sheet was placed on the wound and its perimeter was traced using a permanent marker pen. The tracing was made on the upper sheet; the lower sheet which was in contact with the wounds was disposed after the use. The transparency was placed on metric graph paper that count the amount of 1 $mm^2$ squares. The study drugs i.e. test and the control were provided in a cream base. Both the study drug and control were spread evenly on the burn area with a sterile cotton swab twice daily till the wound healed or till the end of sixth week. Prior to application, basic burn wound management care, like debridement of slough or pus removal, if any was carried out. Quantitative variables were presented as mean values (±SD) and other characters between control and treatment groups were analysed in different ways.

A total of 50 patients were enrolled in both the control and test groups. The study cohort is in Table 6. The primary objective i.e., duration of healing was significantly reduced in Group III (SSD+CHG+rh-EGF 10 µg/g) by more than fifty percent compared to control group. The surface area of the burns in any of the patients both in control and test group (SSD+CHG+rh-EGF 10 µg/g) was no more than 20% total body surface area. The average healing time in the test group was 5 days versus the control group was 12 days.

Second objective i.e., quality of epitheliazation was observed by wound biopsy done after complete healing which showed better epitheliazation in the group III (SSD+CHG+rh-EGF 10 µg/g group) as compared to control group. Adenexal regeneration and collagen maturity were also better as compared to the control areas. There was one case of irritation of wound surface in Group III (SSD+CHG+rh-EGF 10 µg/g), which resolved in 24 hrs without any medication. No significant scar hypertrophy or pigmentary changes we noticed in this group.

TABLE 6

Burn patients study cohort data.

|  | Group-I (Test) | Group-II (Control) | Statistical Inference |
| --- | --- | --- | --- |
| N | 40 | 10 |  |
| Sex (M/F) | 22/18 | 6/4 | Not Significant |
| Age (Years) | 23 ± 4.1 | 27 ± 4.3 | Not Significant |
| Duration of healing (Days) | 5.0 ± 0.6 | 10.6 ± 2.2 | $p < 0.05$ |

TABLE 7

Burn patients study data of wound healing

| Number | 50 |
| --- | --- |
| Sex (M/F) | 28/22 |
| Age | 20 to 35 yrs |
| Average size of Small burn area (in $cm^2$) | 5-40 $cm^2$ |
| Average size of Large burns - BSA (in $cm^2$) | >40 $cm^2$ |
| Average burn wound healing | 95% |
| Average duration of healing | 5 days |

TABLE 8

Range of percentage of wound healing of burn patients in the study

| Percentage of burn area healed | Novel formulations |
|---|---|
| SSD | 70-80% |
| SSD + rh-EGF | 81-90% |
| SSD + rh-EGF + CHG | 91-100% |

From the above results, it is evident that novel synergistic formulation (SSD+CHG+rh-EGF 10 µg/g) accelerates epitheliazation in superficial and partial thickness burns leading to faster burn wound closure, decreased hospital stay and a better prognosis in burn patients. A mounting body of evidence suggests that exogenous growth factors are necessary for tissue repair. They may act as an inducer for endogenous growth factors and their gene expression, or act as a stimulator for tissue repair cells in accelerating wound healing. In a nearly epidemic increasing scenario of burn incidents, sophisticated therapies involving growth factors, such as rh-EGF, which augment clinical healing, are expected to play an important role in future.

Figure 3:
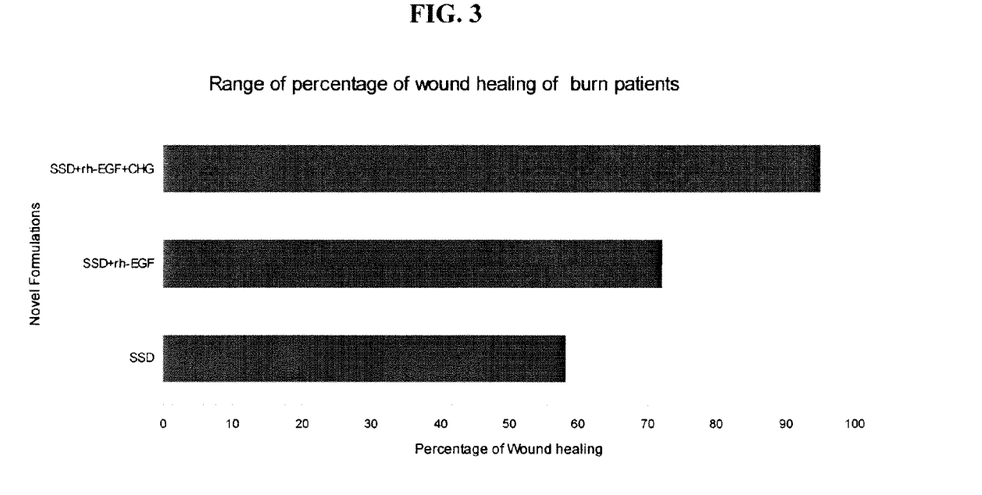
FIG. 3 is a geometrical representation showing the percentage of wound healing of burn patients using different formulation compositions.

FIG. 3 is a geometrical representation of the results shown in table 8 showing the percentage of wound healing in burn patients (human data). The geometrical representation of FIG. 3 confirms that the best wound healing results were obtained with the formulation comprising the SSD+CHG+rh-EGF due to synergistic interaction of the ingredients enhancing each other's antimicrobial and wound healing properties.

The major advantage of this novel synergistic formulation combination is in preventing the infections caused due to the invasion of bacteria at the burn wound and at the same time rh-EGF is healing of the burns without the invasion of bacterial infection, allowing for the quick healing of burns. Besides preventing infection, most important advantage has been the reversal of impaired wound healing due to the effect of SSD, by allowing the exposure of cells to regenerating the tissues to optimal levels in the presence of growth factor rh-EGF. This novel synergistic composition of the formulation is more significant in reduction of infection and thereby allowing the quick wound healing rate and healing of wounds caused by burns. The rationale behind the combination being chlorhexidine gluconate even in low concentrations helps in permeability of silver in burn wounds thereby helping the effectiveness of silver against the resistant micro-organisms.

Example 4

Estimation of rh-EGF in the Novel Formulations rh-EGF was estimated using a solid phase sandwich Enzyme Linked-Immuno-Sorbent Assay (ELISA). A polyclonal antibody specific for human rh-EGF has been coated onto the wells of microtiter strips. Samples, including standards of rh-EGF, control are pipetted into these wells. The main principle is during the first incubation, the rh-EGF antigen binds to the immobilized (capture) antibody on one site. After washing, a biotinylated monoclonal antibody specific for rh-EGF added. During the second incubation, this antibody binds to the immobilized rh-EGF captured during the first incubation. After removal of excess second antibody, Streptavidin-Peroxidase (enzyme) is added. This binds to the biotinylated antibody. After a third incubation and washing to remove all the unbound enzyme, a substrate solution is added, which is acted upon by the bound enzyme to produce colour. The intensity of this coloured product is directly proportional to the concentration of rh-EGF present in the original specimen. Using this method the content of rh-EGF was estimated in the novel formulations mentioned above. The results clearly show that the added content of rh-EGF is same as per the specification and protein is active.

Figure 4:
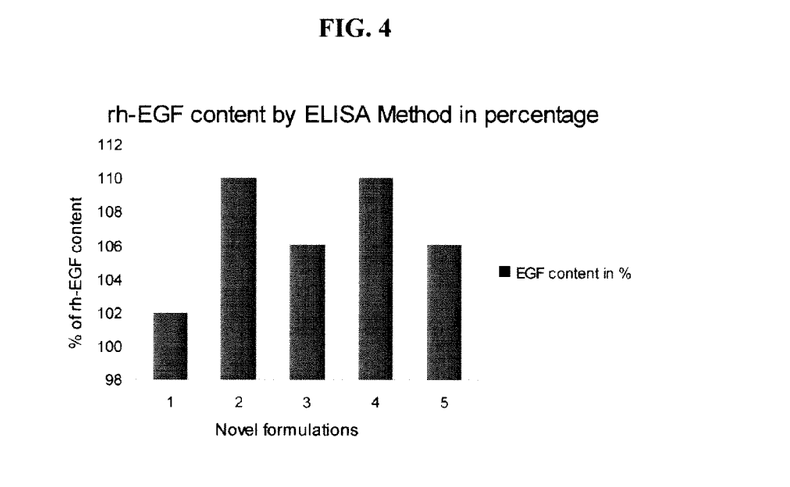
FIG. 4 is a geometrical representation showing estimation of rh-EGF content in novel formulations by ELISA method.

FIG. 4 is a geometrical representation showing the estimation of rh-EGF content in novel formulations by ELISA method explained in example 3 in above paragraphs.

Example 5

Estimation of Silver Sulfadiazine in the Novel Formulations and Estimation of Chlorhexidine Gluconate in the Novel Formulations SSD assay was performed as per the method specified in USP 27 Page No: 1740-1741. Result of these estimation showed that exact amount of SSD added to the cream could be estimated.

CHG assay was also performed as per the procedure specified in BP 2005, BP volume III, Formulation preparations: Specific Monographs Lidocaine and Chlorhexidine gel. Result of these estimation showed that exact amount of CHG added to the cream could be estimated.

Example 6

Kinetics of Synergism with the Novel Formulations

Synergism of rh-EGF of BBIL with SSD and CHG was studies in vitro by analysing the effects of this novel composition on growing cultures of the test organisms. The overnight culture of *Staphylococcus aureus* were used with an $OD_{600}$ value at 0.1 to 0.2. Complete experimental procedure was done by maintaining the temperature conditions at 37° C. The novel synergistic composition having three components namely rh-EGF of BBIL, SSD and CHG was compared with rh-EGF of BBIL and SSD combination. The inoculum time was taken as zero time and after addition of the combination into the culture, the readings were taken at regular time intervals. A graph was plotted with culture optical density versus time for the measurement of kinetics of the novel synergistic formulation. From the results it is concluded that the novel composition having three components namely rh-EGF of BBIL, SSD and CHG was more affective in reduction of the microbial count in comparison with rh-EGF of BBIL and SSD combination. This result clearly indicates the advantage of this novel synergistic combination of rh-EGF of BBIL, SSD and CHG which can be used for burn wounds.

Figure 5:
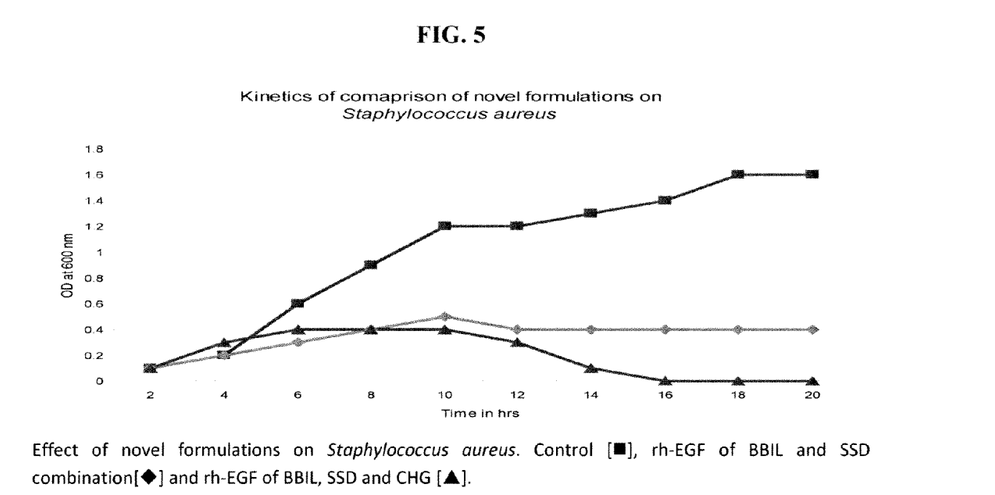
FIG. 5 is graphical representation of kinetics of comparison of novel formulations on *Staphylococcus aureus*.

Referring to FIG. 5 is a graphical representation of kinetics of comparison of novel formulations on *Staphylococcus aureus* as explained in example 6, using the formulations of control (1% SSD), a combination of rh-EGF of BBIL+SSD and combination of rh-EGF of BBIL+SSD+CHG.

Example 7

Stability Studies of Novel Formulation Using the Combination of Silver Sulfadiazine, Chlorhexidine Gluconate and rh-EGF Stability of novel formulations containing SSD, chlorhexidine gluconate and rh-EGF cream was evaluated for Real Time and Accelerated stability conditions. Real Time studies were done at storage temperature of +2° C. to +8° C. for 24 months and Accelerated studies were done at storage temperature of +25° C.±2° C. and 60% RH±5% for 6 months. Rationale behind this stability study is to establish the shelf life of novel formulations containing SSD, chlorohexidine gluconate and rh-EGF cream for 24 months at storage temperature of 2-8° C.

From the results it is concluded that the novel formulations prepared as pharmaceutical composition for use in burn wound are stable for more than two years at storage temperature of 2-8° C.

Figure 6:
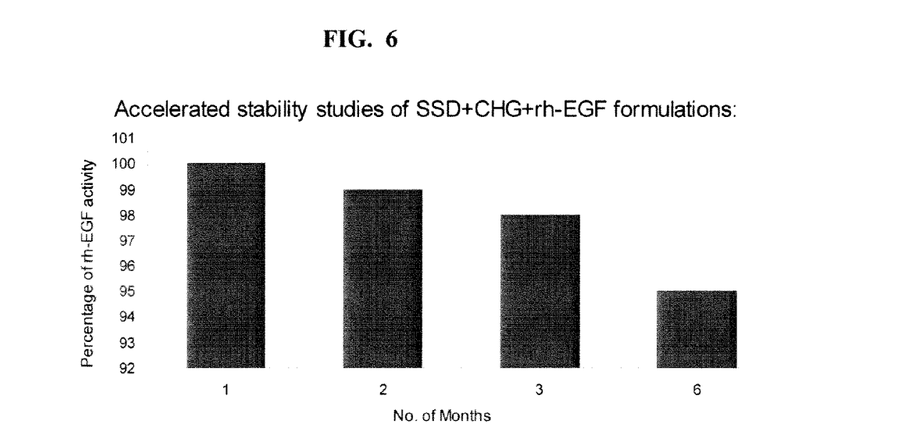
FIG. 6 is a geometrical representation of accelerated stability studies of the formulation of the invention.

FIG. 6 is a geometrical representation showing the accelerated stability studies with the formulation of novel composition of the invention comprising SSD+CHG+rh-EGF. The accelerated stability tests showed that the formulation with novel composition of the invention had 95% rh-EGF activity even after the end of six months. These results established that the novel formulation was stable with 95% or more rh-EGF activity under the accelerated study conditions as explained above in example 7.

Figure 7:
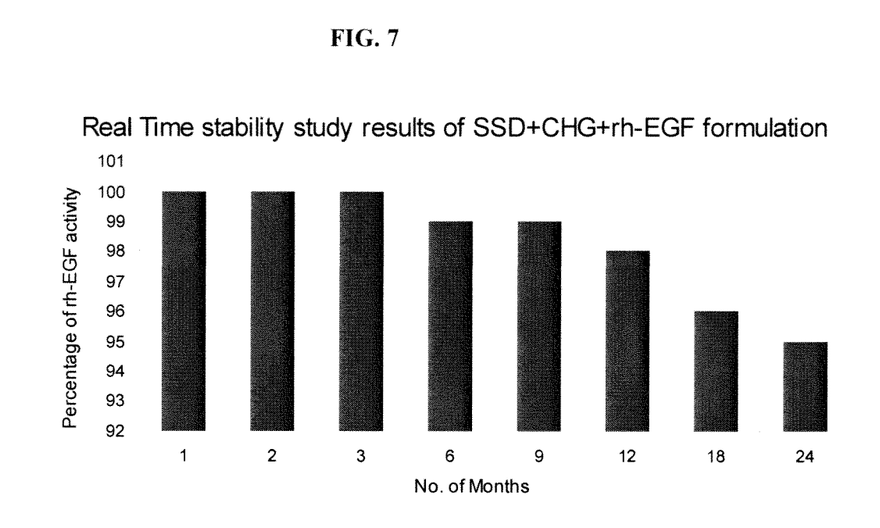
FIG. 7 is a geometrical representation of real time stability studies of the formulation of the invention.

Referring to FIG. 7 is a geometrical representation of real time stability studies done using the novel composition of SSD+CHG+rh-EGF in the formulation. The test results showed that the novel formulation has 95% or more rh-EGF activity even after 24 months under the storage conditions as explained above in example 7. Therefore, the novel formulation is more stable and has a longer shelf life.

Example 8

Preparing Different Formulations for Topical Application Using Novel Compositions of the Invention Different topical cream formulations can be prepared using the novel composition of the invention comprising rh-EGF, SSD and CHG such as herein above described in the foregoing paragraphs, for application in wounds, burn wounds, skin grafts, pressure ulcers, diabetic foot ulcers. The novel composition can be used for preparing the topical formulations wherein other ingredients may be added as a base, carrier, preservative, emulsifiers, skin emollients, soothers and skin softeners etc as per the requirements. Following are the few examples of the cream formulations which can be prepared with varied ingredients in combination with the novel composition of the invention.

It should be understood that the cream formulations given in following tables are only for better understanding of a person skilled in the art and for illustration purposes, showing different embodiments of the invention only. The scope of the claims should not be limited to these cream formulations only, as several other cream formulations may also be prepared in combination of the novel composition of the invention without deviating from the spirit and scope of the invention.

Cream Formulation-1

| | |
|---|---|
| PEG-30 Dipholyhydroxystearate | 1.0% |
| Isohexadecane | 6.0% |
| C-12-15 Alkyl benzoate | 10.0% |
| Titanium dioxide | 10.0% |
| Polyhydroxystearic acid | 10.0% |
| Aluminium stearate | 10.0% |
| Alumina | 10.0% |
| Magnesium sulfate | 1.0% |
| Purified Water | QS |

Cream Formulation-2

| | |
|---|---|
| Stearic acid | 15% |
| Sorbitol | 3.0% |
| Methyl Paraben Sodium | 0.15% |
| Propyl Paraben Sodium | 0.05% |
| Sodium Hydroxide | 0.07% |
| Purified Water | QS |

Cream Formulation-3

| | |
|---|---|
| Disodium EDTA | 0.10% |
| Ammonium acryloyldimethyltaurate/VP copolymer | 0.90% |
| Dipalmitoyl hydroxyproline | 1.0% |
| Bois II ™ | 6.0% |
| Cetyl alcohol | 1.10% |
| C12-15 alkyl benzoate | 5.0% |
| Caprylic/capric triclyceride | 3.0% |
| Tocopheryl acetate | 1.0% |
| Polyacrylamide, C13-14 isoparaffin | 1.0% |
| Ethoxydiglycol | 4.0% |
| Phenoxyethanol, methyl, butyl, ethyl & propylparaben | 1.0% |
| Triethanolamine | QS |
| Purified Water | QS |

Cream Formulation-4 (SLVRGEN™ an Example of the Cream Formulation with Novel Composition of the Invention Comprising rh-EGF+SSD+CHG)

| | |
|---|---|
| Silver Sulfadiazine | 1% |
| Chlorhexidine Gluconate | 0.02% |
| Light liquid paraffin | 10.0% |
| Pemulen TR-1 | 0.5% |
| Carbopol ultrez | 1.3% |
| Sodium Methyl paraben | 0.18% |
| Sodium Propyl paraben | 0.02% |
| Mannitol | 5% |
| Recombinant EGF | 10 µg |
| 20% Triethanolamine | QS |
| Purified water | QS |

REFERENCES

1. Kucan J O. Robson M C, Heggers J P. et al. Comparison of silver sulfadiazine, povidoneiodine and physiologic saline in the treatment of chronic pressure ulcers. *J Am Geriatr Soc.* 1981:29:232-235.
2. McCauley R L, Li Y Y, Chopra V. Herndon D N. Robson M C. Cytoprotection of human dermal fibroblasts against silver sulfadiazine using recombinant growth factors. *J Surg Res.* 1994 April; 56(4):378-84.
3. Vijay Viswanathan, MD, PhD; Sharad Pendsey, MD, MDDG; N. Sekar, MS, MNAMS, MCh, FICS; G. S. R. Murthy, PhD. A Phase III Study to Evaluate the Safety and Efficacy of Recombinant Human Epidermal Growth Factor (REGEN-D™150) in healing Diabetic Foot ulcers. *Wounds* 2006; 18(7): 186-196.
4. Lev-Ran A, Hwang D L: Epidermal growth factor and platelet-derived growth factor in blood in diabetes mellitus. *Acta Endocrinol (copenh)* 1990; 123(3) (September): 326-330.
5. Brown G L. Nannoy L B. Gritten J, Cramer A B, Yancey J M, Curtsinger L J 3$^{rd}$ et al. Enhancement of wound healing by topical treatment with Epidermal growth factor. N Eng J Med 1989; 321(2) (July (13)): 76-9.
6. K. Sharma, P. V. Chemsh Babu, P. Sasidhar, V. K. Srinivas, V. Krishna Mohan, Ella Krishna. Recombinant human epidermal growth factor inclusion body solubilization and refolding at large scale using expanded-bed adsorption chromatography from *Escherichia coli*, Protein Expression and Purification, 2008, 60, 7-14.
7. Greenhalgh, D G. The Role of Growth Factors in Wound Healing. Journal of Trauma-Injury Infection & Critical Care 1996; 41(1): 159-7.
8. Buckley A, Davidson J M, Kamerath C D, Woodward S C. Epidermal growth factor increases granulation tissue formation dose dependently. J. Surg Res. 1987; 43(4) 322-328.
9. Eaglstein W H, Mertz P M, Alvarez O M. Effect of topically applied agents on healing wounds. *Clin Dermatol.* 1984; 2: 112-115.
10. Brown M R W, Wood S M. Relation between cation and lipid content of cell walls of *Pseudomonas aen~ginosa, Proteus~'trlgaris.* and *KlebsieNa aerogenes* and their sensitivity to polymyxin B and other antibacterial agents. *J Pharm Pharmacol.* 1972; 24:215-228.
11. Cooper M L, Boyce S T, Hansbrough J F, et al. Cytotoxicity to cultured human keratinocytes of topical antimicrobial agents. *J Surg Res.* 1990; 48:190-195,
12. Monafo W W, West M A. Current ea ent recommendations for topical burn therapy. *Drugs.* 1990; 40:364-373.
13. Lineaweaver W, McMorris S, Soucy D, Howard R. Cellular and bacterial toxicities of topical antimicrobials. *Plast Reconstr Sulg.* 1985:75:394-j96.
14. Cooper M L. Laxer J A, Hansbrough J F. The cytotoxic effects of commonly used topical antimicrobial agents on human fibroblasts and keratinocytes. *J Trauma.* 1991; 31:775-784.
15. McCauley R L, Linares H A, Pelligrini V, et al. In vitro toxicity of topical antimicrobial agents to human fibroblasts. *J SUT Res.* 1989; 46:267-274.
16. Lindberg R B, Moncrief J A, Mason A D Jr. Control of experimental and clinical burn wound sepsis by topical application of sulfamylon compounds. Ann NY Acad. Sci. 1968; 150:950-960.
17. Taddonio T E, Thomson P D, Smith D J Jr, Prasad J K. A survey of wound monitoring and topical antimicrobial therapy practices in the treatment of burn injury. *J Burn Care Rehabil.* 1990; 11:423-427.
18. LOWBURYE, J. L., LILLEYH, A. & BULL, J. P. 1960 Disinfection of the skin of operation sites. *British Medical Journal* 2, 1039-1044.
19. HAROLD, F. M., BAARDAJ, R., BARON, C & ABRAMS, A. 1969 Dio 9 and chlorhexidine; Inhibition of membrane-bound ATPase and of cation transport in *Streptococcus faecalis. Biochemica et Biophysica Acta* 183, 129-136.
20. Hansbrough J F, Zapata-Sirvent R L, Cooper M L. Effects of topical antimicrobial agents on the human neutrophil resp~ratoryburst. *Arch Sulg.* 1991; 126:603-608.
21. Cason J S, Jackson D M, Lowbury E J, Ricketts C R. Antiseptic and aseptic prophylaxis for burns: use of silver nitrate and of isolators. *Br Med J* 1966; 2(525): 1288-94.
22. Gayle W E, Mayhall C G, Lamb V A, Apollo E, Haynes B W. Resistant *Enterobacter cloacae* in a burn center: the ineffectiveness of silver sulfadiazine. *J Trauma* 1978; 18(5): 317-23.
23. Wenzel R P, Hunting K J, Osterman C A, Sande M A. *Providencia stuartii*, a hospital pathogen: potential factors for its emergence and transmission. *Am J Epidemiol* 1976; 104(2): 170-80.
24. Klasen H J. A historical review of the use of silver in the treatment of burns. II. Renewed interest for silver. *Burns* 2000; 26(2): 131-8.
25. Bridges K, Lowbury E J. Drug resistance in relation to use of silver sulphadiazine cream in a burns unit. *J Clin Pathol* 1977; 30(2): 160-4.
26. Silver S. Bacterial silver resistance: molecular biology and uses and misuses of silver compounds. *FEMS Microbial Rev* 2003; 27(2-3): 341-53.
27. Li X Z, Nikaido H, Williams K E. Silver-resistant mutants of *Escherichia coli* display active efflux of Ag+ and are deficient in porins. *J Bacterial* 1997; 179(19): 6127-32.
28. Fuller F W, Parrish M, Nance F C. A review of the dosimetry of 1% silver sulfadiazine cream in burn wound treatment. J Burn Care Rehabil 1994; 15(3):213-23
29. Ae-Ri Cho Lee, Hyunju Leem, Jaegwan Lee, Kyung Chan Park. Reversal of silver sulfadiazine-impaired wound healing by epidermal growth factor. Biomaterials 2005; 26:4670-4676
30. HUGO, W. B. & LONGWORTHA, R. 1964 Some aspects of the mode of action of chlorhexidine. *Journal of Pharmacy and Pharmacology* 16, 655-662.
31. Annear D I, Mee B J, Bailey M. Instability and linkage of silver resistance, lactose fermentation, and colony structure in *Enterobacter cloacae* from burn wounds. *J Pathol.* 1976; 29(5):441-443.
32. Carr H S, Rosenkranz H S. R factor in *Enterobacter cloacae* resistant to silver sulfadiazine. *Chemotherapy.* 1975; 21(1):41-44.
33. Belly R T, Kydd G C. Silver resistance in microorganisms. *Develop Industrial Microbiol.* 1982; 23:567-577.
34. Choudhury P, Kumar R. Multidrug- and metal-resistant strains of *Klebsiella pneumoniae* isolated from *Penaeus monodon* of the coastal waters of deltaic Sundarban. *Can J Microbiol.* 1998; 44(2): 186-189.
35. Robb E C, Fitz D G, Nathan P. Delivery of topical antimicrobial agents silver sulfadiazine, gentamicin and nystain to infected burn wounds in rats from preloaded synthetic dressings. Trans Am Soc Artif Inter Organs 1980; 26:533-6.
36. Robb E C, Nathan P. Control of experimental burn wound infection: comparative delivery of antimicrobial agent (silver sulfadiazine) either from a cream base or from a solid synthetic dressing. J Trauma 1981; 21:889-93.

The foregoing detailed description of embodiments refers to the accompanying drawings, examples and tables, which illustrate specific embodiments of the invention. Other embodiments having different formulations and compositions do not depart from the scope of the present invention. The term "the invention" or the like is used with reference to certain specific examples of the many alternative aspects or embodiments of the applicant's invention set forth in this specification, and neither its use nor its absence is intended to limit the scope of the applicant's invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing "references" and description is for the purpose of illustration only, and not for the purpose of limitation.

We claim:

1. A topical pharmaceutical formulation consisting of:
   a) 1% silver sulfadiazine;
   b) 5-15 μg recombinant human epidermal growth factor (rh-EGF);
   c) 0.02% chlorhexidine gluconate (CHG); and
   d) one or more inactive ingredients selected from the group consisting of polyethylene glycol-30 (PEG-30), dipolyhydroxystearate, isohexadecane, C-12-15 alkyl benzoate, titanium dioxide, polyhydroxystearic acid, aluminium stearate, alumina, magnesium sulphate, stearic acid, sorbitol, methyl paraben sodium, propyl paraben sodium, sodium hydroxide, disodium EDTA, ammonium acryloyldimethylaurate, dipalmitoyl hydroxyproline, cetyl alcohol, C12-15 alkyl benzoate, caprylic/capric triglyceride, tocopheryl acetate, polyacrylamide, C13-14 isoparaffin, ethoxydiglycol, phenoxyethanol, triethanolamine, light liquid paraffin, pemulen TR-1, carbopol ultrez, mannitol, and purified water; wherein the topical pharmaceutical formulation is in the form of a cream or a gel or a liquid.

2. The topical pharmaceutical formulation of claim 1 which is a topical formulation in the form of a cream and having 5 μg rh-EGF/g cream.

3. The topical pharmaceutical formulation of claim 1 which is a topical formulation in the form of a cream and having 10 μg rh-EGF/g cream.

4. The topical pharmaceutical formulation of claim 1 which is a topical formulation in the form of a cream and having 15 μg rh-EGF/g cream.

5. The topical pharmaceutical formulation of claim 1 which is a topical formulation in the form of a gel and having 5 μg rh-EGF/g gel.

6. The topical pharmaceutical formulation of claim 1 which is a topical formulation in the form of a gel and having 10 μg rh-EGF/g gel.

7. The topical pharmaceutical formulation of claim 1 which is a topical formulation in the form of a gel and having 15 μg rh-EGF/g gel.

8. The topical pharmaceutical formulation of claim 3 wherein the inactive ingredients are 10% light liquid paraffin, 0.5% pemulen TR-1, 1.3% carbopol ultrez, 0.18% sodium methyl paraben, 0.02% sodium propyl paraben, 5% mannitol, 20% triethanolamine, and purified water.

9. A topical pharmaceutical formulation consisting of:
   a) 1% silver sulfadiazine;
   b) 5-15 μg recombinant human epidermal growth factor (rh-EGF);
   c) 0.02% chlorhexidine gluconate (CHG); and
   d) one or more inactive ingredients selected from the group consisting of carriers, preservatives, emulsifiers, and skin emollients wherein the topical pharmaceutical formulation is in the form of a cream or a gel or a liquid.

10. The topical pharmaceutical formulation of claim 9 which is a topical formulation in the form of a cream and having 5 μg rh-EGF/g cream.

11. The topical pharmaceutical formulation of claim 9 which is a topical formulation in the form of a cream and having 10 μg rh-EGF/g cream.

12. The topical pharmaceutical formulation of claim 9 which is a topical formulation in the form of a cream and having 15 μg rh-EGF/g cream.

13. The topical pharmaceutical formulation of claim 9 which is a topical formulation in the form of a gel and having 5 μg rh-EGF/g gel.

14. The topical pharmaceutical formulation of claim 9 which is a topical formulation in the form of a gel and having 10 μg rh-EGF/g gel.

15. The topical pharmaceutical formulation of claim 9 which is a topical formulation in the form of a gel and having 15 μg rh-EGF/g gel.

* * * * *